(12) United States Patent
Florio

(10) Patent No.: US 6,324,427 B1
(45) Date of Patent: Nov. 27, 2001

(54) IMPLANTABLE CARDIAC STIMULATION DEVICE HAVING T-WAVE DISCRIMINATION OF FUSION EVENTS DURING AUTOCAPTURE/ AUTOTHRESHOLD ASSESSMENT

(75) Inventor: Joseph J. Florio, La Canada, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/237,617

(22) Filed: Jan. 26, 1999

(51) Int. Cl.$^7$ ................................................. A61N 1/362
(52) U.S. Cl. ................................................................ 607/28
(58) Field of Search .................................. 607/9, 14, 27, 607/28

(56) References Cited

U.S. PATENT DOCUMENTS

| | | |
|---|---|---|
| 3,949,758 | 4/1976 | Jirak . |
| 4,228,803 | 10/1980 | Rickards . |
| 4,556,062 | 12/1985 | Grassi et al. . |
| 4,557,266 | 12/1985 | Schober . |
| 4,674,508 | 6/1987 | DeCote . |
| 4,674,509 | 6/1987 | DeCote . |
| 4,686,988 | 8/1987 | Sholder . |
| 4,708,142 | 11/1987 | DeCote . |
| 4,712,555 | 12/1987 | Thornander et al. . |
| 4,729,376 | 3/1988 | DeCote . |
| 4,817,605 | 4/1989 | Sholder . |
| 4,880,004 | 11/1989 | Baker et al. . |
| 4,913,146 | 4/1990 | DeCote . |
| 4,940,052 | 7/1990 | Mann . |
| 5,161,529 | 11/1992 | Stotts et al. . |
| 5,222,493 | 6/1993 | Sholder . |
| 5,309,919 | 5/1994 | Snell et al. . |
| 5,350,410 | 9/1994 | Kleks et al. ............................ 607/28 |
| 5,431,691 | 7/1995 | Snell et al. .............................. 607/27 |
| 5,456,692 | 10/1995 | Smith, Jr. et al. ...................... 607/31 |
| 5,476,487 | 12/1995 | Sholder ................................. 607/28 |
| 5,534,016 | * 7/1996 | Boute ...................................... 607/9 |

* cited by examiner

*Primary Examiner*—Scott M. Getzow

(57) ABSTRACT

A system and method for discriminating a fusion beat from an evoked response during the autocapture/autothreshold routines of an implantable stimulation device is provided. The presently disclosed system and method reliably verifies capture in an implantable stimulation device by accurately discriminating a fusion beat from an evoked response based on an analysis and comparison of the morphology, amplitude, polarity, pattern and/or timing intervals of resulting T-waves. The disclosed system for discriminating a fusion beat includes a pulse generator; a means for sensing voltage signals evidencing depolarization and repolarization of cardiac tissue; and a microprocessor based means for determining, based on an analysis of the subsequent T-waves, whether a voltage signal that occurs during the capture detection window is a depolarization voltage signal, which evidences capture, or a fusion beat.

17 Claims, 8 Drawing Sheets

IMPLANTABLE CARDIAC STIMULATION DEVICE HAVING T-WAVE DISCRIMINATION OF FUSION EVENTS DURING AUTOCAPTURE/ AUTOTHRESHOLD ASSESSMENT

FIELD OF THE INVENTION

The present invention relates to implantable medical devices and methods, and more particularly to an implantable cardiac stimulation device, such as an implantable pacemaker or an implantable cardioverter/defibrillator that provides a method for discriminating fusion events and non-fusion events during operation of autocapture/ autothreshold routines by monitoring changes in the T-wave.

BACKGROUND OF THE INVENTION

Implantable pacemakers generate electrical stimulation pulses and deliver such stimulation pulses to atrial and/or ventricular muscle tissue of a patient's heart at a prescribed rate when, through disease or other causes, the heart is not able to maintain the prescribed heart rate on its own. "Capture" of the patient's heart occurs when the applied electrical stimulus generated by the pacemaker is of sufficient energy to stimulate or depolarize the cardiac muscle tissue, thereby causing a cardiac contraction thereby forcing the heart rate or rhythm to track the delivery of the electrical stimuli. A capture event is typically represented by an evoked R-wave of an intercardiac electrogram (IEGM) signal. Capture fails to occur when the applied stimulus is of insufficient energy to stimulate or depolarize the cardiac tissue and the heart rate is not controlled by the pacemaker. This is also referred to as a "loss-of-capture" event. Needless to say, for a cardiac pacemaker to properly perform its intended function, it is critically important that the electrical stimuli it issues be of sufficient energy to capture the heart, i.e., to cause the cardiac tissue to depolarize.

The energy of the electrical stimuli generated by an implanted pacemaker is derived from the energy stored in the pacemaker battery. The pacemaker battery has a limited amount of energy stored therein, and the generation of electrical stimuli represents by far the greatest drain of such energy. In order to preserve this limited energy and prolong the life of the pacemaker battery, it is known in the art to adjust the energy of the delivered electrical stimuli so that it is just sufficient to cause capture, with an appropriate safety margin. See, e.g., U.S. Pat. Nos. 3,949,758 and 4,686,988. The amount of energy needed to effectuate capture is known as the capture "threshold", and electrical stimuli of energy less than the capture threshold do not bring about capture, while electrical stimuli of energy greater than the capture threshold do bring about capture. Many recent generation pacemakers also include autocapture and autothreshold features that enable the value of the capture threshold of a given patient to be regularly determined, thereby enabling the output energy of the pacemaker stimulus to be optimally set to an autocapture value that is above the capture threshold, but not too far above the capture threshold, so as to conserve the energy in the pacemaker battery.

Reliably determining capture within an implantable pacemaker is not an easy task. Some implantable pacemakers perform a Capture Verification Routine on a continuing basis and take remedial actions whenever a loss-of-capture occurs. Other Capture Verification Routines are performed by the implantable pacemaker on a periodic basis to automatically maintain the capture threshold at an appropriate value. It will be appreciated that these "autocapture" routines, therefore, are critical to maximize the effectiveness and efficiency of the pacemaker. Recent generation implantable pacemakers typically initiate their autocapture routine, if not on a regular basis, then when two or more successive loss-of-capture events occur. When this happens, the autocapture routine instructs the pacemaker to incrementally increase the energy of the output stimulus until capture occurs. As a safety precaution, a high output backup stimulus is provided, whenever there is a detected loss-of-capture, in order to maintain the cardiac rhythm of the patient.

Another feature commonly found in recent generation implantable pacemakers is an "autothreshold" routine which is periodically employed to ensure that the energy level of stimulation pulses are as low as possible in order to conserve the pacemaker's battery power, but high enough to safely insure capture. During an autothreshold routine the implantable pacemaker decrements the energy of its output stimulus until capture is lost. The output energy is then incrementally increased until capture is regained. As with the autocapture routine, every loss-of-capture of the primary output stimulus is typically followed by a high output back-up stimulus in order to maintain the cardiac rhythm of the patient during the process. Because of their similar functions, the autocapture and autothreshold routines of a pacemaker are usually conducted in conjunction or even simultaneously with each other. Thus, the term "autocapture/autothreshold" routine will be used herein to refer to either or both an autocapture routine or an autothreshold routine.

The presence of fusion events or fusion beats during operation of autocapture/autothreshold routines can introduce anomalies into the intercardiac electrogram (IEGM) data used by those routines to verify capture. A fusion beat is typically a ventricular or atrial depolarization that starts from two foci, one spontaneous and the other a result of pacemaker stimulus. Fusion beats can result in the magnification, diminishment or abolition of the R-wave of the sensed voltage signal. If magnified, the voltage signal could be misclassified as an evoked signal, resulting in the pacemaker missing a loss-of-capture event and defining the autocapture and/or autothreshold value as lower than it actually is. Conversely, if the R-wave of the sensed voltage signal is diminished or abolished by the fusion beat, the pacemaker may incorrectly identify the signal as a loss-of-capture, resulting in autocapture/autothreshold values being set higher than the actually are.

What is needed, therefore, is a very reliable method of discriminating between capture and loss-of-capture in an implantable pacemaker and, more particularly, a method of determining whether a response sensed during an autocapture/autothreshold routine is a fusion beat, which may or may not be indicative of capture, or is an evoked response. When a fusion beat is identified during the autocapture/autothreshold routines, the corresponding IECG data should be identified appropriately and the routines repeated to the extent necessary to make a clear determination of capture or loss-of-capture.

The classical approach to determine capture during the autocapture/autothreshold routines is to apply a ventricular stimulus (V-pulse) of varying output energy (i.e., amplitude and/or width) in order to search for the capture threshold. The implantable pacemaker looks for an evoked R-wave response with each and every V-pulse applied. The evoked R-wave response is typically monitored within 5–100 msec of the V-pulse (i.e., within a prescribed time window after the issued V-pulse, generally referred to as the "capture detection window") to determine if the issued V-pulse caused capture. If no ventricular evoked response is sensed, a subsequent ventricular "backup" pulse may be issued, and the search for the capture threshold continues. If a ventricular response is sensed, then the pacemaker circuits assume that the capture threshold is less than the energy of the most-recently issued V-pulse, and thereafter sets the V-pulse energy to an appropriate value above such threshold.

Several related art methods of capture verification are disclosed, for example, in U.S. Pat. Nos. 4,686,988, 4,817,605, and 5,222,493 (all of Sholder and each incorporated in its entirety by reference herein) which deal with sensing the evoked response using various sensing configurations and a special evoked response (ER) amplifier. None of these patents disclose methods of discriminating fusion beats nor do they recognize that capture can be determined from an evaluation and analysis of the T-wave and the V-pulse to T-wave time interval.

In U.S. Pat. Nos. 4,674,508; 4,674,509; 4,708,142; 4,729,376; and 4,913,146 (all of DeCote, Jr. and each incorporated in its entirety by reference herein), the autocapture and capture-determining methods involve issuing a double stimulation pulse, separated in time by less than the natural refractory period of the heart. Hence, at most only one of the pulses can induce cardiac capture. DeCote Jr. teaches subtracting the post-pulse lead recovery artifacts (50 msec following pulse) for both pulses. In the absence of capture, such post-pulse artifacts are essentially identical, and the difference is zero. If capture occurs, however, the post-pulse artifacts are significantly different, and the difference is not zero. Again, none of these patents disclose methods of discriminating fusion beats from the post-pulse artifacts nor do they recognize that capture can be determined from an evaluation and analysis of the T-wave characteristics.

Still other related art is disclosed in U.S. Pat. No. 5,350,410 issued to Kleks et al. and also incorporated in its entirety by reference herein. In the Kleks et al. disclosure the Capture Verification Routine also uses double pulses, but uses a more sophisticated technique than the aforementioned DeCote Jr. techniques for digitally analyzing and comparing the evoked response after the pulses. See also U.S. Pat. No. 5,766,229 (Bornzin) issued Jun. 16, 1998, incorporated in its entirety by reference herein, which teaches that capture should be verified only infrequently, and only when the heart rhythm is stable. The Bornzin disclosure describes a method of capture verification that involves shortening the cycle length significantly from that of the stable rhythm, which advantageously reduces the likelihood of fusion.

The T-wave is mostly ignored in prior art patents that rely on the IEGM signal for sensing when certain cardiac events occur. In many instances, the existence of the T-wave in the IEGM signal is regarded as a nuisance. A few related art patents, however, do rely on the T-wave for certain purposes. For example, U.S. Pat. No. 4,556,062 issued to Grassi et al., incorporated in its entirety by reference herein, discloses the use of the slope of the T-wave as an indication of what the basic stimulation frequency of a rate-responsive pacer should be.

In addition, U.S. Pat. No. 4,228,803, issued to Rickards and incorporated in its entirety by reference herein, teaches measuring the time interval between the stimulus pulse and the following T-wave. Variation in such stimulus to T-wave interval is then used as a parameter to control the pacemaker escape interval, thereby adjusting the pacing rate as a function of the stimulus to T-wave interval. There are also several related art references that utilize the mere sensing of the T-wave or T-wave parameters to aid in the verification of capture. These related art references include U.S. Pat. No. 5,161,529 issued to Stottes et al.; U.S. Pat. No. 4,880,004 issued to Baker Jr. et al.; and U.S. Pat. No. 4,557,266 issued to Schober; each of which is incorporated in its entirety by reference herein.

More recently, the T-wave has been used as part of a Capture Verification Routine as disclosed in U.S. Pat. No. 5,476,487 (Sholder), issued Dec. 19, 1995, the disclosure of which is incorporated by reference herein. The Sholder patent teaches a method of determining capture or lack-of-capture by measuring the stimulus-to-T-wave time period rather than looking for an evoked response immediately following application of the V-pulse. In particular, it looks for a significant change in the stimulus-to-T-wave time for a series of ventricular pulse pairs, where the first pulse of each pair has decreasing energy from that of a first pulse of a prior pair, and the backup pulse of each pair is always of sufficient energy to cause capture. The time interval between the first stimulus to the T-wave is compared to a reference value for a given patient. If there is a significant change in this time interval, then the first pulse is assumed to have lost capture and any resulting T-wave occurred due to the backup pulse. Thus, the Sholder patent teaches capture or loss-of-capture based on a change in the stimulus to T-wave interval.

None of these references or applications recognizes that, during an autocapture/autothreshold routine, variations in the T-wave morphology, pattern and/or stimulus to T-wave time interval may be used to determine whether a sensed voltage signal, occurring during the capture detection window, is an event signifying capture, signifying a fusion event or signifying loss-of-capture. Thus, the occurrence of fusion events during autocapture/autothreshold routines continues to result in inefficient and potentially dangerous adjustments to a pacemaker's operational parameters, as such fusion events are mistaken either for evoked responses to a stimulation pulse or for a loss-of-capture event.

SUMMARY OF THE INVENTION

The present invention addresses the above and other needs by providing a method for discriminating a fusion beat from an evoked response in an implantable cardiac stimulating device, especially during the autocapture/autothreshold routines of the device, based on an analysis of one or more attributes of T-waves.

Also provided herein are implantable cardiac stimulating devices employing this method. In particular, the disclosed method involves analyzing the stimulus to T-wave time interval, the morphology and/or the pattern of T-waves that occur during execution of the autocapture/autothreshold routines to determine whether a voltage waveform sensed in response to a stimulation pulse is the result of capture or is a fusion event.

To discriminate between an evoked response (i.e., capture) and a fusion beat (or fusion event), at least one attribute of the T-wave following the sensed voltage waveform, such as, the stimulus to T-wave time, the morphology and/or the pattern of the T-wave, is analyzed. If the measured value of the T-wave varies less than a predetermined amount from the value of the same attribute of a reference T-wave, then the voltage waveform is identified as a ventricular evoked response, signifying capture. If, on the other hand, the measured value of the T-wave attribute varies from the value of the attribute for the reference T-wave by more than the predetermined amount, the voltage waveform is identified as a fusion event, and the autocapture/autothreshold routine is modified to cure the fusion problem.

Advantageously, the present invention may also be used to reliably determine whether a loss-of-capture event or fusion event has occurred when no voltage signal has been detected during the capture detection window. This loss-of-Capture Verification Routine is performed by continuing the pacemaker's sensitivity to voltage signals for a specified period following the termination of the capture detection window. If a voltage signal (T-wave) is detected during this time period, it is assumed that the lack of detectable voltage signal during the capture detection window was the result of a fusion beat and the pacemaker initiates its fusion event recovery routine. If, on the other hand, no T-wave is detected following termination of the capture detection window, then it is assumed that an actual loss-of-capture has occurred and the pacemaker initiates its Loss-Of-Capture Recovery Routine.

A preferred method provided herein, for discriminating a fusion beat from an evoked response during the autocapture/autothreshold routines of an implantable pacemaker involves the steps of: (1) defining at least one select attribute (i.e. stimulus to T-wave time, morphology and/or pattern) of a reference T-wave; (2) sensing a voltage signal during the capture detection window of autocapture/autothreshold routines; (3) measuring the at least one attribute of the T-wave that immediately follows the sensed voltage signal; and (4) classifying the sensed voltage signal as either a true evoked response, if the attribute(s) of the measured T-wave has not varied from the attribute(s) of the reference T-wave by more than a prescribed amount, or classifying the sensed voltage signal as a fusion beat, if the attribute(s) of the measured T-wave has varied from the attribute(s) of the reference T-wave by more than the prescribed amount.

The present invention may also be characterized as a capture/threshold assessment system for use within an implantable pacemaker. The system including: a pulse generator; a sensing circuit for sensing voltage signals evidencing depolarization and repolarization of cardiac tissue; and a microprocessor based system for characterizing the voltage signals sensed during the autocapture/autothreshold routines based on an analysis of sensed T-waves. The microprocessor based system is particularly adapted for first defining a capture detection window that lasts a prescribed time interval following the generation of a stimulus pulse and for determining whether a voltage signal that occurs during the capture detection window is a depolarization voltage signal, which evidences capture, or is a fusion beat.

For example, in a preferred embodiment, the microprocessor based system is capable of defining at least one attribute of a reference T-wave, such as, its morphology, pattern and/or stimulus-to-T-wave time interval; analyzing the at least one attribute of a sensed T-wave that follows the depolarization voltage signal sensed during the capture detection window; and classifying the voltage signal that is sensed during the capture detection window as a depolarization voltage signal or as a fusion beat based on a comparison of the value of the attribute of the reference T-wave to the same attribute of the sensed T-wave. The microprocessor based system classifies the voltage signal that is sensed during the capture detection window as a depolarization voltage signal whenever the measured attribute(s) of the sensed T-wave has not varied substantially from the same attribute(s) of the reference T-wave. Conversely, the microprocessor based system classifies the voltage signal that is sensed during the capture detection window as a fusion beat whenever the measured attribute(s) of the sensed T-wave has varied substantially from that of the reference T-wave.

Accordingly, it is an aspect of the present invention to provide a technique for reliably distinguishing a fusion beat from an evoked response based on an analysis of at least one attribute of the T-wave, and preferably analysis of more than one attribute, such the morphology, pattern and/or timing interval of the T-wave.

It is another aspect of the present invention to provide a microprocessor based capture/threshold assessment system that accurately and reliably detects fusion beats during an autocapture/autothreshold routine. Advantageously, the detection of fusion beats during such a routine dramatically reduces the likelihood of the pacemaker setting an output voltage below threshold and/or recording a threshold that is lower than the actual threshold at that point in time.

In yet another aspect, the present invention can, advantageously, provide a reliable technique and system for detecting the presence of fusion beats at any time during pacing operation. The continuing presence of fusion beats may prompt a programmatic change to the pacing rate of the implantable pacemaker or to the programmed delay intervals (i.e. AV interval) associated with the programmed pacing rate.

Thus, the method provided herein, by identifying the presence of fusion beats prevents such disadvantageous programmatic changes.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Provided herein is a system and method of distinguishing evoked responses from fusion beat events by analyzing one or more attributes of the T-wave that follows the evoked response or fusion beat.

Most cardiac stimulating devices are designed to periodically or continually monitor the effectiveness of the stimulation V-pulses issued therefrom. Normally, this is done by establishing a time period, the capture detection window, during which the pacemaker is sensitive to the voltage waveforms emanating from the heart muscle. The time period is generally selected such that only the first waveform following the stimulation V-pulse is detected, and when such a waveform is detected, it is assumed that the waveform is the evoked QRS complex, evidencing ventricular depolarization and, therefore capture.

It is possible, however, that this first-detected waveform is in fact an artifact of a fusion beat, rather than an evoked QRS complex. Thus, the method provided herein looks to the second waveform, known as the T-wave, following the stimulation V-pulse, when a first waveform has been detected, and then analyzes the T-wave waveform to determine whether the first detected waveform was in fact an evoked response or a fusion beat event.

In one aspect, the method provided herein involves establishing an acceptable value range for one or more attributes of the patient's T-waves, i.e. the reference T-wave values; sensing the T-wave following the first-detected waveform that follows the stimulation V-pulse; measuring the same one or more attributes of the sensed T-wave that have been established for the reference T-wave; comparing the values of the sensed T-wave attributes to those of the reference T-wave; and determining whether the attribute values of the sensed T-wave are within the acceptable value range of the reference T-wave. If the sensed T-wave attribute values are within the acceptable range, it is determined that the first-detected waveform was an evoked response. If the attribute values are not within the acceptable range, it is determined that the first-detected waveform was a fusion event.

To better understand how the present invention may be practiced, it will first be helpful to review the main components, and basic operation, of a pacing system. Accordingly, the following overview of a pacemaker is presented.

Figure 1:
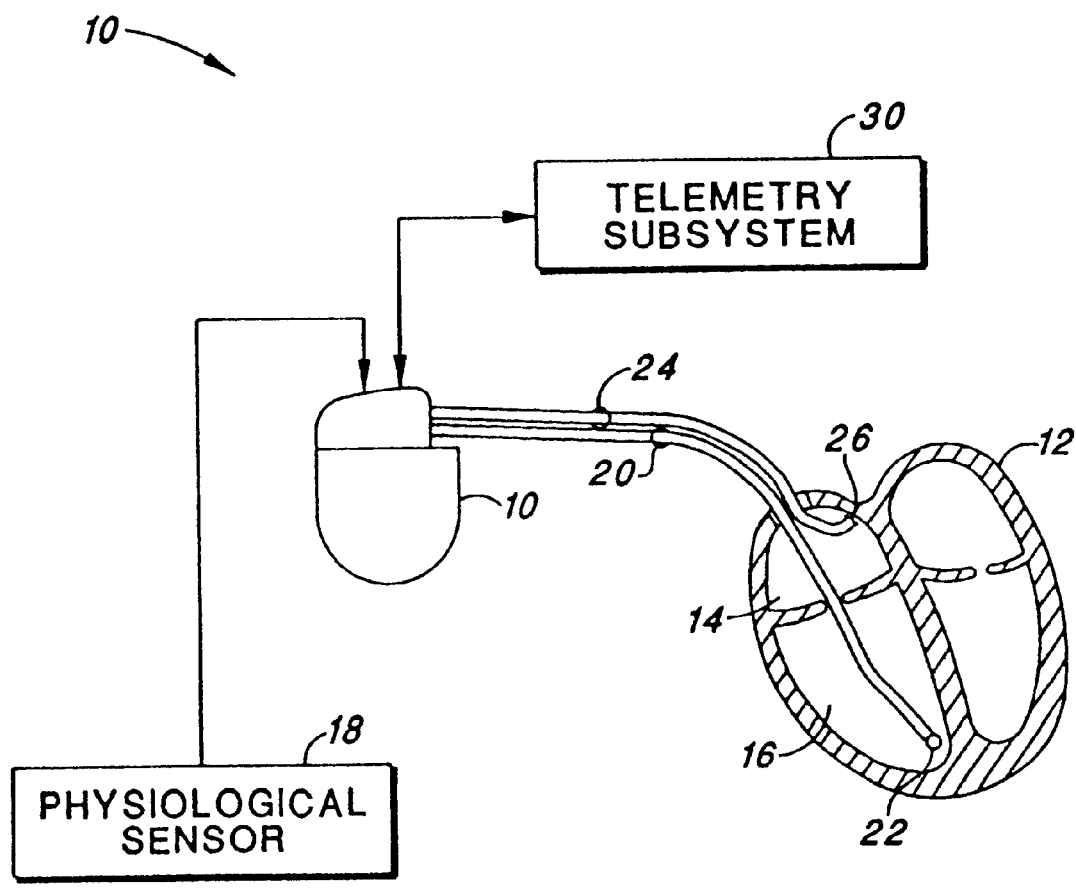
FIG. 1 shows an implantable pacemaker coupled to the heart of a patient.

In FIG. 1, there is shown an implantable pacemaker 10 coupled to a patient's heart 12. The implantable pacemaker 10 is a small, battery-powered, controllable device that is programmed to monitor the activity of the patient's heart 12 and to provide stimulation pulses to the atrium 14 and ventricle 16 of the patient's heart 12 as necessary to maintain a prescribed heart rhythm or rate. The implantable pacemaker 10 may also have a physiological sensor 18 associated therewith. A common type of sensor is an activity sensor, realized, for example, using a piezoelectric element that is mounted inside of the case of the pacemaker, which senses the physical activity of the patient. However, not all pacemakers have a physiological sensor 18 incorporated therein, and such sensor is by no means required for practicing the present invention. As is well known to those of skill in the art, a pacemaker that is capable of adjusting, on demand, the rate of stimulation pulses, as a function of one or more sensed physiological parameters, is known as a rate-responsive pacemaker.

The implantable pacemaker 10 shown in FIG. 1 is a dual-chamber pacemaker. This means that sensing and/or pacing may occur in both chambers of the heart 12, i.e., in the atrium 14 and/or the ventricle 16. While the present invention is primarily intended for use with a dual-chamber pacemaker 10, the basic principle of the invention (avoiding mis-identification of fusion beats as evoked responses and vice versa during autocapture/autothreshold routines) can be practiced using a single-chamber pacemaker, where sensing and pacing occur in only one chamber, e.g., the ventricle, of the heart.

The preferred dual-chamber pacemaker 10 is coupled to a heart 12 by way of a pair of pacing leads 20 and 24. One pacing lead 20 has an electrode 22 positioned in the right ventricle 16 of the heart 12. This lead 20 is thus typically referred to as the ventricular lead, and the signals generated by the pacemaker 10 for delivery to the heart 12 through the electrode 22 over this lead 20, or the signals sensed through the electrode 22 and the lead 20, are processed by circuits in what is known as the ventricular channel of the pacemaker 10. Similarly, a second pacing lead 24 has an electrode 26 positioned in the right atrium 14 of the heart 12. This second lead 24 is thus typically referred to as the atrial lead, and the signals generated by the pacemaker 10 for delivery to the heart 12 through the electrode 26 over the atrial lead 24, or the signals sensed through electrode 26 and the atrial lead 24, are processed by circuits in what is known as the atrial channel of the pacemaker 10.

The pacemaker also preferably includes a telemetry subsystem 30 for transmitting data and parameter values to an external telemetry receiver, and for receiving telemetry data instructions and the like from an external programmer or other telemetry transmitter. The manner of establishing and operating a telemetry link between an external programmer and implantable medical device is well known in the art. Data instructions received from the external programmer are typically stored in the pacemaker memory associated with the control system and are adapted to control the general operation of the pacemaker.

It is noted that the control system of the pacemaker may take numerous forms, any of which is suitable for purposes of the present invention. The details of the control system, whether based on a microprocessor, state machine, or other type of control device, or simulated control device, are not critical to an understanding or implementation of the present invention, and hence are not presented herein. Such details may be found in the literature. See, e.g., U.S. Pat. No. 4,712,555, incorporated in its entirety by reference herein, wherein a state-machine type of operation for a pacemaker is described. What is important for purposes of the present invention, as explained fully below, is that the control system of the pacemaker be capable, in conjunction with other pacemaker circuitry, of measuring and comparing the morphology, pattern, and/or time intervals of various T-waves.

The preferred embodiment of a pacemaker adapted for use with the present invention utilizes a microprocessor that is controlled by an appropriate programmed set of instructions in the pacemaker memory. Using a microprocessor in this fashion to control a pacemaker is known in the art, as described, e.g., in U.S. Pat. Nos. 5,309,919; 4,940,052; 5,431,691; and 5,456,692; each of which is incorporated in its entirety by reference herein. U.S. Pat. Nos. 5,309,919 and 5,456,692 are particularly relevant for teaching a method of implementing a microprocessor-controlled pacemaker which can be adapted for sensing voltage signals in the patient's heart and for determining whether the voltage signals are indicative of a fusion event or an evoked response.

Figure 2:
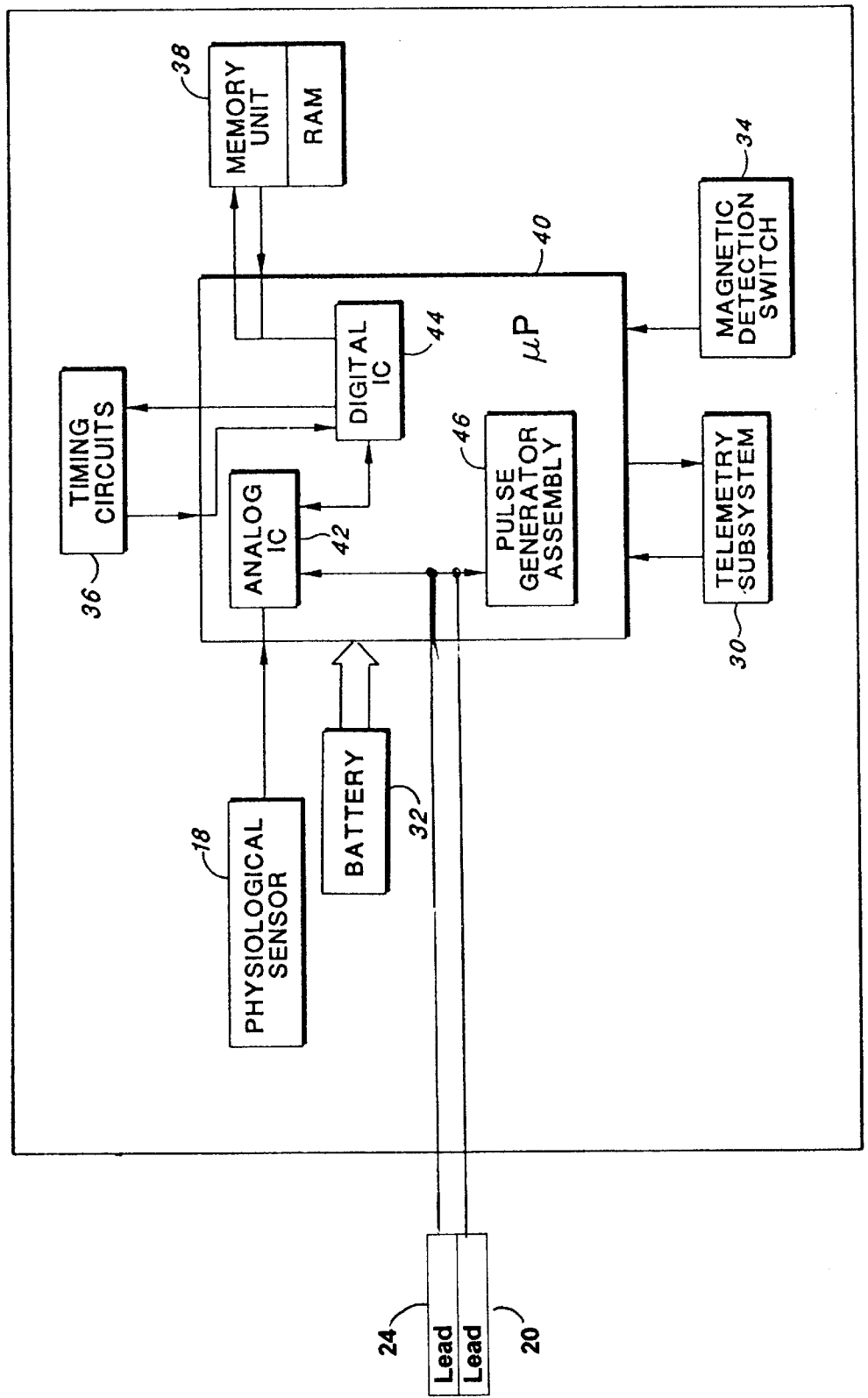
FIG. 2 is a block diagram of a representative microprocessor-based implantable pacemaker that may be used with the present invention.

With the above overview in mind, reference is next made to FIG. 2 where there is shown a more detailed functional block diagram of the preferred implantable pacemaker 10. As seen therein, the preferred microprocessor based pacemaker includes a battery 32, physiological sensor 18, atrial and ventricular leads 20 and 24, atrial and ventricular amplifiers (embedded in the analog IC), a magnetic detection switch/reed switch 34, crystal oscillator and associated timing circuits 36, a telemetry subsystem 30 (i.e. communication coil), and a microprocessor 40 with memory 38. The microprocessor 40 further includes an Analog IC 42, Digital IC 44, Pulse Generator Assembly 46, and a sufficiently large RAM 38, schematically arranged, as shown in FIG. 2. In the preferred embodiment, the microprocessor 40 includes the timing circuits 36 and the magnetic detection switch 34. These elements are shown separately in FIG. 2 only to highlight the separate timing functions and magnetic detection functions performed by the pacemaker.

Figure 3:
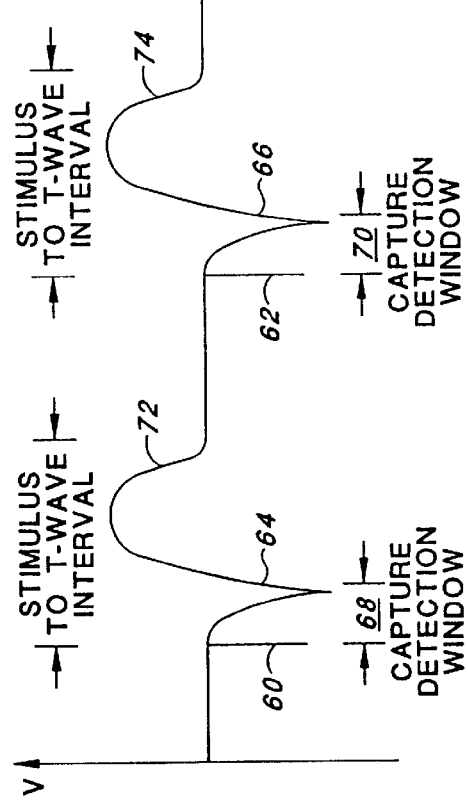
FIGS. 3 and 4 illustrate timing waveform diagrams that conceptually illustrate how the present invention discriminates a fusion event from an evoked response.
Figure 4:
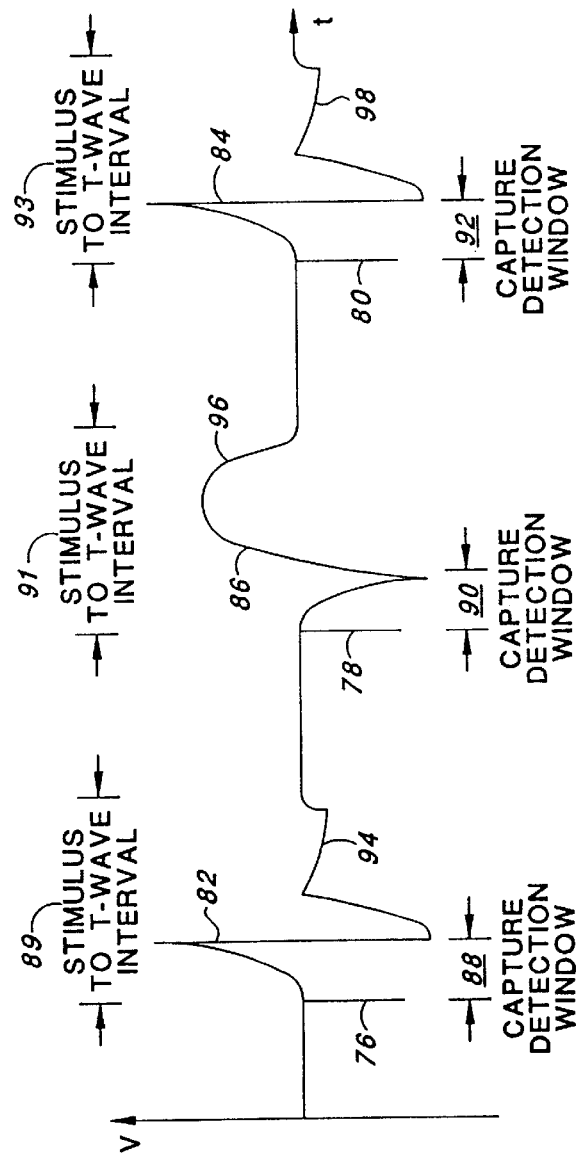

In FIGS. 3 and 4, there are shown timing waveform diagrams that conceptually illustrate one way in which the present invention may discriminate an evoked response from a fusion event during an autocapture/autothreshold routine. The diagram of FIG. 3 depicts key cardiac events that occur during a typical ventricular pacing cycle. The cardiac events illustrated in FIG. 3 appear as such events might appear in an intracardiac electrogram (IEGM) signal, with time being represented along the horizontal axis. Thus, the pacing cycle, for purposes of FIG. 3, is defined as the time interval between ventricular stimuli, i.e., the time interval between a first V-pulse 60 and a second V-pulse 62. Thus, for a heart paced to beat at a rate of 60 beats per minute (bpm), the time interval would be 1000 milliseconds (1 second). (Note: atrial events, e.g., P-waves and/or A-pulses are not depicted in FIGS. 3 or 4.)

As depicted in FIG. 3, each V-pulse 60 and 62 is of sufficient energy to capture the cardiac tissue. Hence, immediately following each V-pulse 60 and 62, there is an evoked R-wave 64 and 66, respectively. The R-wave represents depolarization of the ventricular muscle tissue. Depolarization of the muscle tissue, in turn, causes the ventricular tissue to physically contract, thereby pumping blood (which is, of course, the function of the heart).

Also shown in FIG. 3, is a period of time, or "window" of time, referred to as the capture detection window. It is during this capture detection window, e.g., the zone 68 following V-pulse 60, and the zone 70, following V-pulse 62, that an evoked response is most likely to occur. Typically, the capture detection window lasts between about 5 msec and 100 msec following the generation of the V-pulse. A T-wave 72, 74 follows the evoked response 64, 66, respectively, of a capturing V-pulse 60, 62, respectively. A T-wave always follows a depolarization of the cardiac tissue. The T-wave evidences the repolarization of the ventricular tissue. During the time period that follows depolarization up until the time the T-wave occurs in the cardiac pacing cycle, the ventricular muscle tissue is refractory, i.e., it is incapable of contracting because it is just recovering from a depolarization or contraction. Thus, the time interval from the evoked response R-wave 64 or 66 to the occurrence of the T-wave 72 or 74, respectively, comprises a repolarization time. Assuming that an applied V-pulse captures the ventricles, this repolarization time interval will be approximately equal to the time interval between the V-pulse and the resulting T-wave.

In FIG. 4, a waveform is depicted that might occur during a ventricular pacing cycle in the presence of fusion events or fusion beats. As defined above, a fusion event or fusion beat is a depolarization that starts from two foci, one spontaneous or intrinsic and the other a result of the pacemaker stimulation V-pulse. When fusion occurs, the waveform may either be mis-identified as an evoked response, when in fact no capture has occurred, or it may be mis-identified as a loss-of-capture event, when in fact capture was achievable. This is because the depolarization caused by the stimulation V-pulse and the intrinsic depolarization can either complement one another, resulting in a detectable waveform during the capture detection window, or the two depolarizations may essentially "cancel" each another, resulting in a smaller detectable waveform during the capture detection window. In either case, it is impossible to know whether the issued stimulation V-pulse was of sufficient energy to capture the heart muscle because its effects were thwarted by the intrinsic depolarization. Thus, especially in the case of a detected waveform occurring during the capture detection window, analysis of the subsequent T-wave ensures that the detected waveform was indeed an evoked response and not a fusion beat event.

In the present method, if a signal is detected in the capture detection window, then the T-wave is evaluated to determine if the sensed signal was a "true" evoked response. If a T-wave is detected that is smaller (within a predefined percentage) than the reference T-wave, then it is concluded that fusion occurred and the rate is increased to overdrive the fusion beats. If a T-wave is detected that is within an acceptable range of the reference T-wave, then it is concluded that an evoked response occurred and capture threshold assessment continues.

If no signal is detected in the capture detection window, then it is concluded that a "true" loss-of-capture has occurred, a back-up stimulation pulse is immediately issued and the output energy of the stimulation V-pulse. In the preferred embodiment, at least two consecutive "true" loss-of-captures must occur before the output energy of the stimulation pulses is incrementally increased.

As shown in FIG. 4, fusion event waveforms 82, 84, that may be mistaken for evoked responses, and a true evoked-response waveform 86 are illustrated. Each waveform 82, 84, 86 is proceeded by a stimulation V-pulse 76, 78, 80, respectively, and each waveform 82, 84, 86 occurs during the respective capture detection window, 88, 90, 92. It is during these capture detection windows 88, 90, 92 that the Capture Verification Routines typically look to determine whether capture or loss-of-capture has occurred. Thus, conventional capture verification techniques would mistakenly assume that all three V-pulses 76, 78, 80 achieved capture because of the presence of a waveform in the respective capture detection windows 88, 90, 92.

The present method discriminates between a fusion event and an evoked response by looking at the subsequent T-waves 94, 96, and 98, respectively. As indicated above, a T-wave represents the repolarization of the ventricular tissue and always follows a depolarization of the cardiac tissue. The time interval from the V-pulse 76, 88, or 80 to the occurrence of the T-wave 94, 96, or 98 is referred to as the stimulus to T-wave interval 89, 91, 93. The stimulus to T-wave interval and/or other attributes of the T-wave, such as the morphology, amplitude, polarity or pattern, can be used to distinguish a fusion beat from a true evoked response. For any capture event in a given patient, the resulting T-wave attributes have been found to be very consistent and repeatable parameters. Thus, whenever a true evoked response occurs after a V-pulse, the variance in such T-wave attributes for a particular patient is minimal. It is this non-variance in T-wave attributes that forms the basis of discriminating between a fusion beat and an evoked response during the capture verification process. Where the variance between the actual T-wave attributes and the expected attributes is significant, the "capture event" is identified instead as a fusion event.

The elements of the pacemaker that are preferably used to establish the present capture threshold assessment system include the pulse generator assembly, timing circuits, atrial and/or ventricular amplifiers capable of detecting voltage signals that are indicative of the depolarization and repolarization of the cardiac tissues, and a control system (most preferably a microprocessor) for controlling the operation of the pacemaker through a set of programmed instructions. In particular, the microprocessor is adapted to execute, on a periodic or demand basis, an autocapture/autothreshold routine. The autocapture part of the routine refers to a capture verification process whereby the implantable pacemaker adjusts the output energy of the stimulation pulses in order to insure the pulses are of sufficiently high energy to cause capture of the patient's heart. The autothreshold portion of the routine is periodically invoked in an effort to optimize the stimulation pulses to both provide capture of the heart and conserve the limited supply of battery power. Under this routine, for example, the output energy of the stimulation pulses is incrementally decreased until capture is lost then incrementally increased until capture is restored.

In the typical implantable pacemaker having autocapture/autothreshold routines, the routines allow the pacemaker to adjust the pulse width and pulse amplitude of the stimulation pulses, preferably within the ventricular channel. By means of the adjustment in stimulation pulse magnitude, the autocapture/autothreshold routines optimize the power consumption of the pacemaker, yet maintain a suitable capture threshold safety margin. In addition, the autocapture and/or autothreshold routine includes a mechanism to provide a backup stimulation pulse of sufficient magnitude to cause capture when any loss-of-capture event is detected during the power consumption optimization sequence.

In the flowcharts of FIGS. 5–9, each main step of the method is depicted in a "box" or "block", with each block having a reference numeral assigned thereto for reference purposes. The autocapture/autothreshold routine operates in conjunction with the programmed pacing mode of the implantable stimulation device, e.g., an implantable pacemaker, or an implantable cardioverter-defibrillator device.

Figure 5:
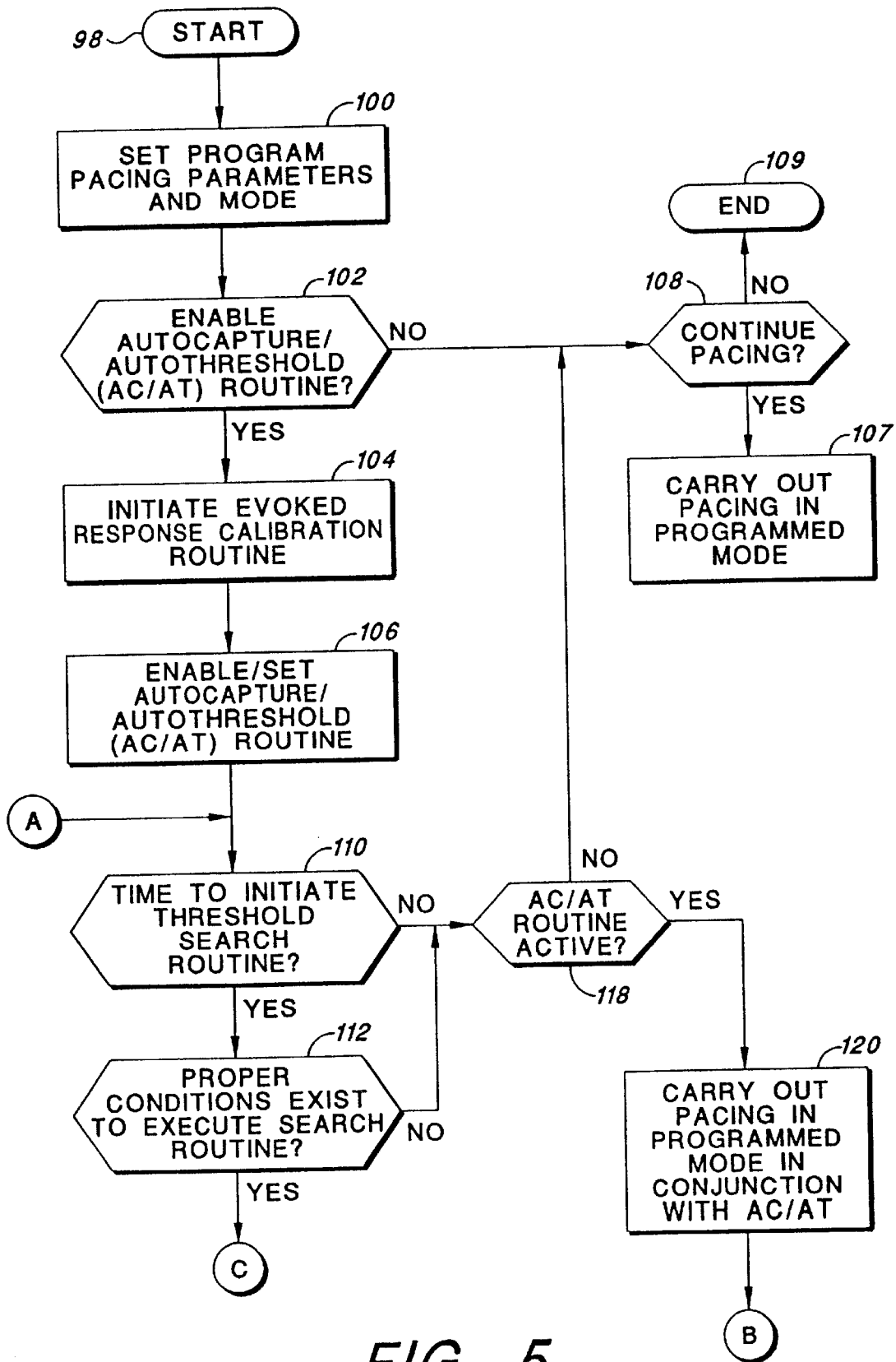
FIGS. 5, 6 and 7 are a flowchart of a preferred autocapture/autothreshold routine.
Figure 6:
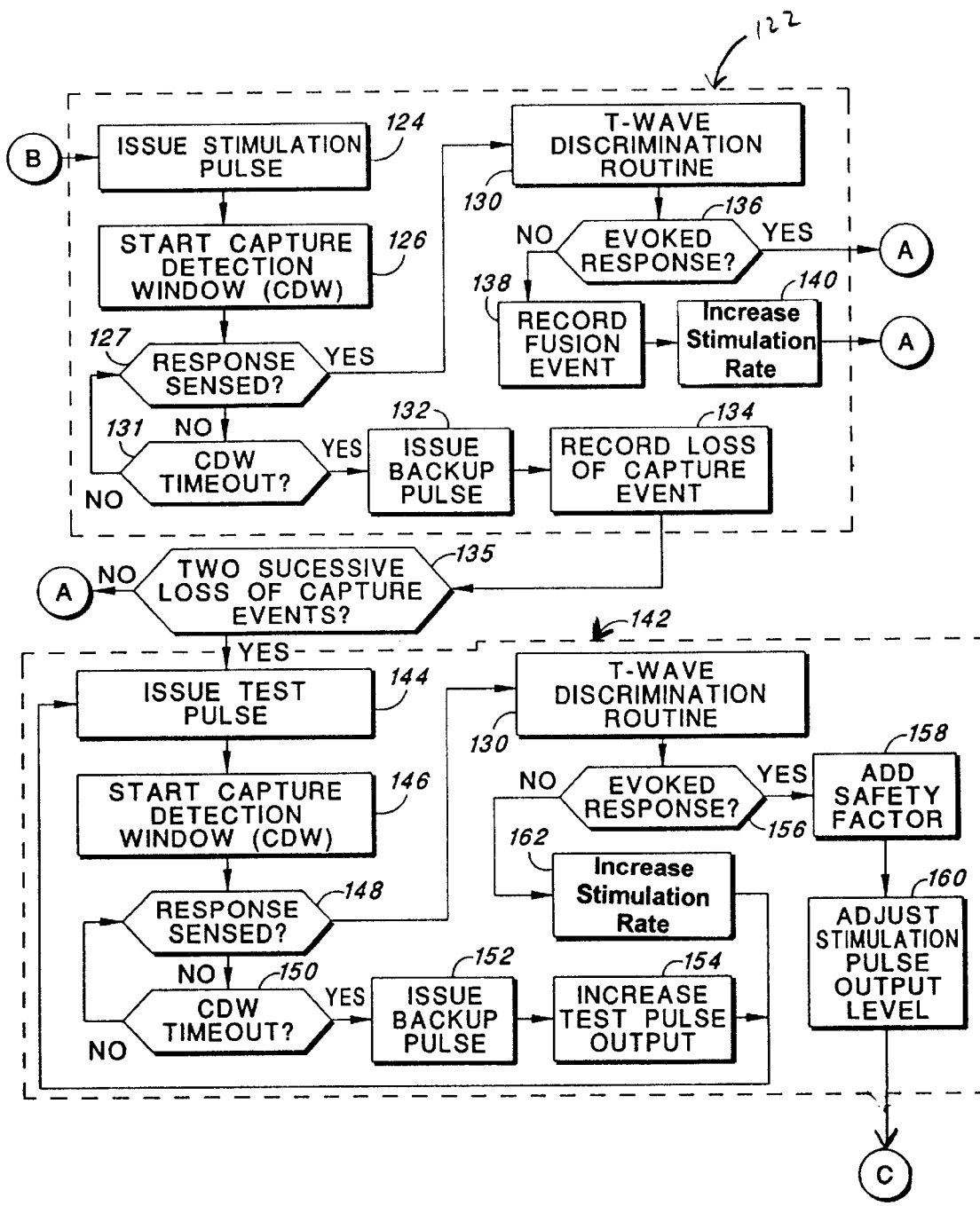
Figure 7:
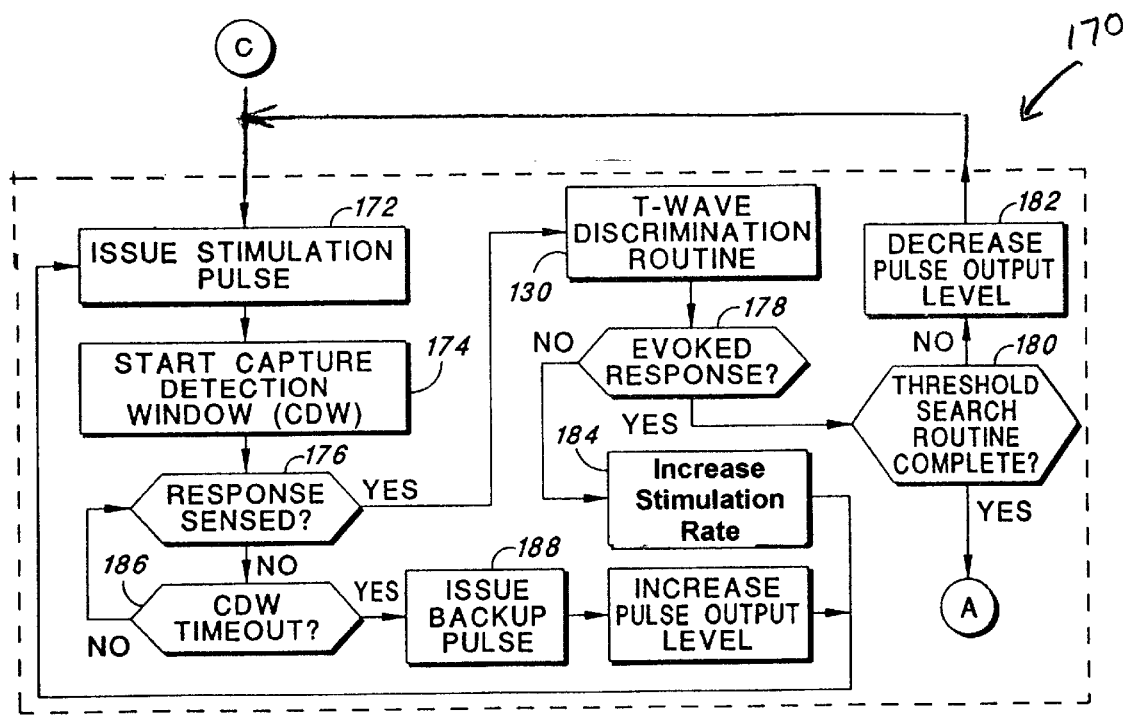

FIGS. 5, 6 and 7 present a flowchart of an exemplary autocapture/autothreshold routine incorporating the new method described herein. This routine is merely exemplary, as will be appreciated by those of skill in the art. Any pacemaker routine, designed to determine whether a stimulus has resulted in an evoked response, may employ the method and/or apparatus described herein, and thereby determine whether a sensed response was an evoked response or a fusion event.

As seen in these figures the exemplary autocapture/autothreshold routine includes a variety of initiation steps coupled with four major sub-routines that operate either continually or on a periodic basis. The four major sub-routines include: Evoked Response Calibration Routine (104 of FIG. 5); Capture Verification Routine (122 of FIG. 6); Loss-of-Capture Recovery Routine (142 of FIG. 6); and Autothreshold Search Routine (170 of FIG. 7).

At the start (block 98) of the process, as depicted in FIG. 5, it is assumed that the pacemaker is operating in a desired programmed mode and that all of the pacing parameters needed by the pacemaker to operate in its desired program mode have been set (block 100).

In addition to conventional pacing parameters, parameters relating to practicing the present invention are preprogrammed and include a definition of how much the primary V-pulse is decreased or increased in energy during the relevant portions of the autocapture/autothreshold routine, how often the periodic Autothreshold Search Routine is to be invoked (e.g., once a day, every 90 minutes), and a safety factor. The safety factor is used during the Loss-Of-Capture Recovery Routine as well as during the Autothreshold Search Routine and defines how much above the determined capture threshold the ventricular stimulus energy is to be set. While these preprogrammed parameters are relevant to the present invention they are also relevant to the general operation of the pacemaker and thus are set using routine methods, well known to those of skill in the art.

Assuming, then, that all of the pacing parameters have been set (block 100), a first determination is made as to whether the autocapture/autothreshold routine is to be enabled (block 102).

If the autocapture/autothreshold routine has not been enabled (NO branch of block 102), the pacemaker resumes cardiac pacing in the desired programmed mode (block 107) if pacing is still required (blocks 108 and 109).

If it has been enabled (YES branch of block 102), the process initiates the Evoked Response Calibration Routine (block 104). The Evoked Response Calibration Routine (block 104) adjusts the evoked response detection sensitivity after measuring the polarization caused by a pacing pulse delivered during the natural refractory period of the heart. As seen in FIG. 5, the Evoked Response Calibration Routine (block 104) is executed prior to enabling the autocapture/autothreshold routine (block 106) in order to adjust the sensitivity of the atrial and ventricular amplifiers.

After the autocapture/autothreshold routine has been enabled (block 106), the next determination that is made is whether it is time to initiate (block 110) a periodic running of the Threshold Search Routine. Typically, the Threshold Search Routine (block 170 of FIG. 7) will start automatically at a specified frequency, e.g., once or twice every 8–12 hours, or 3–6 times every day. Also, the Threshold Search Routine (block 170 of FIG. 7) may be triggered by command from an external programmer, or upon the occurrence of certain events within the pacemaker.

If it is time to start the Threshold Search Routine (YES branch of block 110), then a first step is to verify that the proper conditions exist to accurately perform the Threshold Search Routine (block 112). In general, such conditions require that the pacemaker be engaged in ventricular pacing (generating V-pulses) at a rate that is stable (e.g., when the patient is at rest). It is noted that in the preferred embodiment, the Threshold Search Routine (block 170) is suspended whenever the patient's pacing rate is over 100 pulses per minute (ppm).

If the pacemaker is engaged in ventricular pacing, a determination is made as to whether there is sensed patient activity. Sensed patient activity can readily be determined if the pacemaker is a rate-responsive pacemaker by simply checking the sensor-indicated-rate (SIR) signal generated by the pacemaker's physiological sensor. If the pacemaker is a dual-chamber pacemaker, capable of sensing naturally occurring P-waves, patient activity may also be sensed by simply looking at the P-wave rate. If the P-wave rate is high, e.g., greater than 100 pulses per minute (ppm), then that indicates the patient is probably exercising (or engaging in some other not-at-rest activity). If patient activity is sensed, then that suggests the patient is not at rest and the proper conditions for executing the threshold search program do not exist (NO branch of block 112). As such, the Threshold Search Routine is delayed for a prescribed amount of time, during which delay the pacemaker continues to operate in its programmed mode. If patient activity is not sensed, then the proper conditions for performing the autothreshold assessment process have been verified and the autothreshold procedure begins. Details of the Threshold Search Routine (block 170) are provided below.

If it is not time to commence the Threshold Search Routine (NO branch of block 110), then the next determination is whether the autocapture/autothreshold routine is active (block 118). If the autocapture/autothreshold routine is not active or not in use (NO branch of block 118), the pacemaker simply continues to pace in its programmed mode (See blocks 107, 108, and 109). If, however, the autocapture/autothreshold routine is active and is in use (YES branch of block 118), the pacemaker proceeds to run the Capture Verification Routine in conjunction with the desired pacing mode (block 120).

When initiated, the Capture Verification Routine (block 122, as shown in FIG. 6) is a continuously running program that performs a loss-of-capture criteria test for each stimulation pulse generated during the programmed pacing sequence. The loss-of-capture criteria test used within the Capture Verification Routine (block 122) is initiated with the generation of a stimulation pulse (block 124), and preferably a V-pulse. The Capture Verification Routine (block 122) then starts a capture detection window (block 126) that lasts a prescribed time interval following the generation of the stimulus pulse. The routine then determines whether a voltage signal occurs or other response is sensed during the capture detection window (block 127). If so (YES branch of block 127), the T-wave Discrimination Routine is invoked (block 130) and the attributes of the subsequent waveforms are measured to determine whether the first sensed voltage signal was a depolarization voltage signal, which evidences capture, or some other signal such as a fusion beat.

If there is no voltage signal or other response detected during the capture detection window (NO branch of block 127), then the Capture Verification Routine (block 122) generates a backup stimulation pulse (block 132) after the capture detection window has elapsed or timed out (block 131). The amplitude and pulse width of the back-up stimulation pulse is of sufficient magnitude to cause capture which maintains the patient's heart rhythm. The actual magnitude of the backup stimulation pulse (block 132) may be a function of the current capture threshold. The backup stimulation pulse (block 132), if needed, is delivered immediately after the capture detection window has elapsed (block 131). The capture detection window preferably lasts between about 60 msec and about 100 msec after the primary stimulation pulse (block 124). After the back-up pulse has been generated (block 132), the event is recorded as a loss-of-capture event (block 134).

Alternatively, as described in detail below, a enhanced Loss-Of-Capture Verification Routine (block 142 of FIG. 6) may be employed to determine whether an actual loss-of-capture event or fusion event has occurred.

Assuming the event was a loss-of-capture and was an isolated event (YES branch of block 135), i.e. less than two successive loss-of capture events, the microprocessor then resumes pacing in the prescribed programmed mode while checking to see if it is time to run the Threshold Search Routine (block 110).

As indicated in the above description, if a response is sensed during the capture detection window (YES branch of block 127), then the T-wave Discrimination Routine is initiated (block 130), which is described in more detail below. If the T-wave Discrimination Routine (block 130) identifies the response as a "true" evoked response (YES branch of block 136), the Capture Verification Routine (block 122) continues the pacing in accordance with the programmed pacing mode. If, however, the T-wave Discrimination Routine (block 130) identifies the response as a fusion beat or fusion event (NO branch of block 136), it is logged as such (block 138) in the pacemaker memory unit and the stimulation rate is increased be a predetermined amount so as to overdrive the intrinsic rate (block 140). The pacemaker then continues the programmed pacing routines.

If "n" successive loss-of-capture events have occurred (YES branch of block 135) (where "n" is preferably at least 2), the Loss-of-capture Recovery Routine (block 142) is then performed. The Loss-of-capture Recovery Routine (block 142) is adapted to incrementally increase a test pulse output and determine whether the prescribed capture acceptance criteria are met which is indicative of capture. Specifically, the Loss-Of-Capture Recovery Routine (block 142) is initiated with the generation of a test pulse output (block 144) which then starts the capture detection window (block 146).

If a voltage signal or response is sensed during the capture detection window (YES branch of block 148), the Loss-Of-Capture Recovery Routine may then invoke the T-wave Discrimination Routine (block 130).

When a response is not sensed during the capture detection window (NO branch of block 148) and the capture detection window has elapsed or timed-out (block 150), a backup pulse is generated (block 152) and the test pulse output is then incrementally increased (block 154) and another test pulse is generated at the incrementally increased level (Return to block 144). Incrementally increasing the test pulse output (block 154) preferably involves adjusting the test pulse amplitude, the test pulse width, or both. The correct pulse amplitude and pulse width needed to ensure safe pacing of the patient's heart are determined by repeating this process at incrementally increased test pulse output levels until a test pulse output of sufficient magnitude is found that ensures capture.

The capture acceptance criteria used during the execution of this routine involves analyzing the attributes of waveforms following the detection of a voltage signal in the capture detection window. Thus, it is important to determine whether the voltage signal that occurs during the capture detection window immediately following the test pulse is a depolarization voltage signal, which evidences capture, or a fusion beat, which may or may not evidence capture.

As with the Capture Verification Routine, the enhanced Loss-Of-Capture Recovery Routine, shown in FIG. 6, preferably utilizes the T-wave Discrimination Routine (block 130) as part of the capture acceptance criteria to identify the presence of a fusion beat.

If the T-wave Discrimination Routine (block 130) identifies the response as a "true" evoked response (YES branch of block 156) and the Loss-Of-Capture Recovery Routine (block 142) determines that the test pulse output is of sufficient magnitude to ensure capture, a safety factor is then added to the test pulse output level (block 158) in order to provide an additional margin of safety. The resulting value (test output level assuring capture plus safety value) is then used as the stimulation pulse output level during subsequent pacing operations (block 160).

If, however, the T-wave Discrimination Routine identifies the response as a fusion beat or fusion event (NO branch of block 156), the Loss-Of-Capture Recovery Routine (block 142) does not adjust the output level of the test pulse but instead increases the stimulation rate so as to override the intrinsic rate (block 162) and instead, repeats the test at the previous output level until the fusion beat is absent (Return to block 144).

As shown in FIG. 7, the Threshold Search Routine (block 170) is preferably performed as soon as the Loss-Of-Capture Recovery Routine (block 142) is complete. The Threshold Search Routine (block 170) uses a combination of capture acceptance criteria and loss-of-capture criteria to determine the pacing threshold. During the Threshold Search Routine (block 170), the pacemaker first decreases the amplitude and pulse width of the output stimulus until capture is lost. The output is then incrementally increased until capture is regained to determine the threshold value. Only after capture has been lost and then regained is the threshold search program complete.

In particular, the Threshold Search Routine (block 170) first generates a stimulation pulse at a prescribed level (block 172). The capture detection window is started (block 174) and the routine then determines whether a response or voltage signal is sensed during the capture detection window (block 176).

If a response is sensed (YES branch of block 176), the Threshold Search Routine may initiate the T-wave Discrimination Routine (block 130) which either verifies that the sensed response was an evoked response (YES branch of block 178) or identifies the response as a fusion beat (NO branch of block 178).

If the T-wave discrimination invoked during the Threshold Search Routine identifies the response as a fusion beat (NO branch of block 178), the Threshold Search Routine does not adjust the output level of the pulse but instead increases the stimulation rate so as to override the intrinsic rate (block 184) and repeats the test at that same output level (Return to block 172).

If, however, the Threshold Search Routine identifies the response as an evoked response (YES branch of block 178), the Threshold Search Routine decreases the output level of the pulse (block 182) and issues a stimulation pulse at the new level (block 172) until the evoked response is absent (no at block 176 ), thereby indicating capture threshold has been attained. The Threshold Search Routine continues this process until the threshold search is complete.

Once complete (Yes branch of block 180), a determination is made whether to continue pacing in accordance with the desired programmed mode or to end the autocapture/ autothreshold routine.

In the event that no response was sensed during the capture detection window (NO branch of block 176), and the capture detection window has elapsed (block 186), the pacemaker then issues a back-up stimulation pulse (block 188). As with the earlier described sub-routines, every loss-of-capture of the primary output stimulus is typically followed by a high output backup stimulus in order to maintain the cardiac rhythm of the patient during the Threshold Search Routine.

Alternatively, as described below, an enhanced Loss-Of-Capture Verification Routine may be employed to determine whether an actual loss-of-capture event, or a fusion beat has occurred. Assuming a loss-of-capture has occurred, the Threshold Search Routine then incrementally increases the pulse output level and generates another stimulation pulse at the incrementally increased level (Return to block 172).

As indicated above, the Threshold Search Routine can also be programmed to be executed at a prescribed frequency such as once every 90 minutes or once every 24 hours. Since the Threshold Search Routine utilizes both capture acceptance criteria as well as loss-of-capture criteria, it is important to properly identify fusion beats. Again, the T-wave Discrimination Routine is employed to identify a fusion beat that may occur during the capture detection window.

From the above discussion it is seen that three of the four sub-routines included as part of the typical autocapture/ autothreshold routine, as exemplified herein, may include the T-wave Discrimination Routine described and claimed herein. This T-wave Discrimination Routine, described in detail below, distinguishes a response sensed during the capture detection window as an evoked response or a fusion event.

Figure 8:
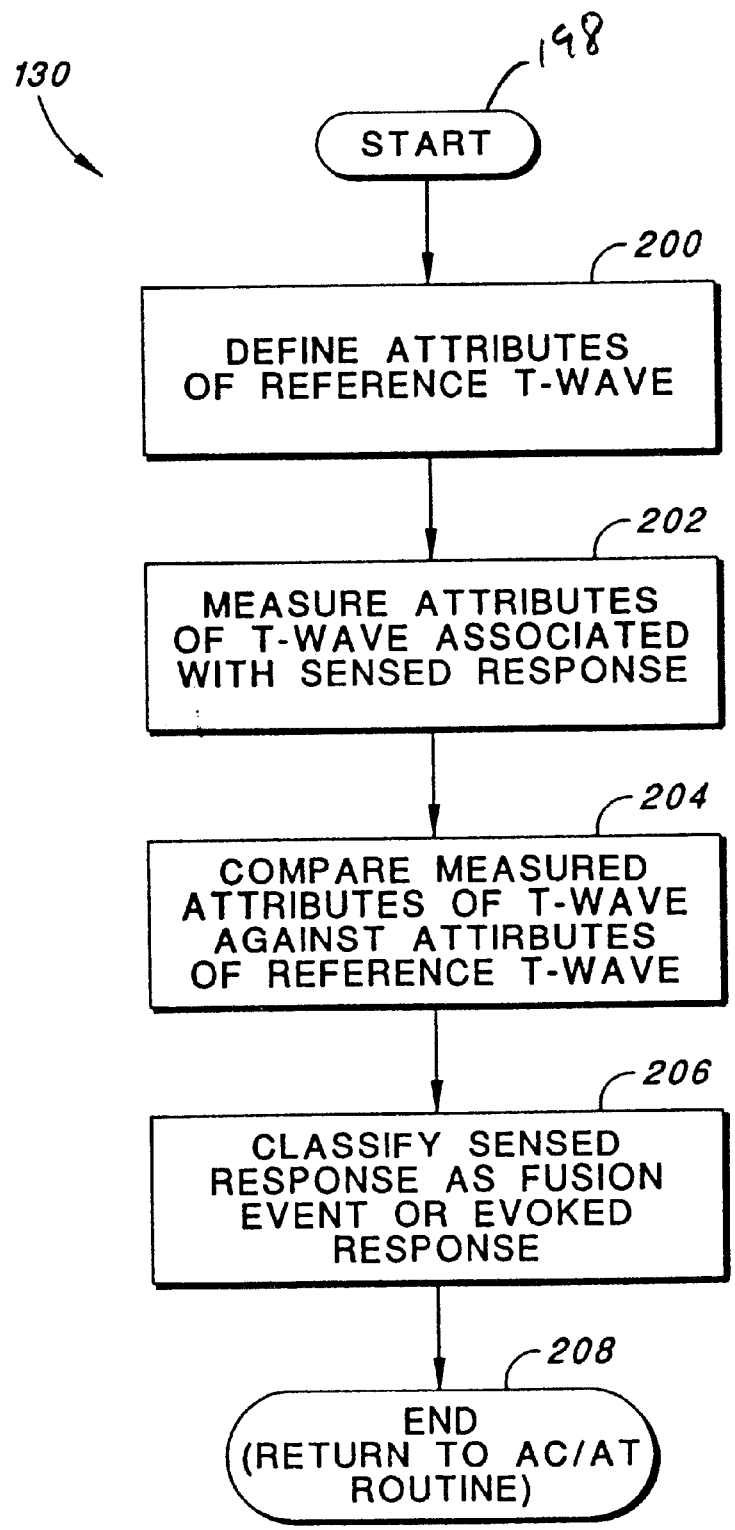
FIG. 8 is a flowchart generally illustrating a preferred T-wave Discrimination Routine in accordance with the present invention.

Referring next to FIG. 8, there is shown a general flowchart of the preferred T-wave Discrimination Routine as contemplated herein. FIG. 8

As seen in the block diagram of FIG. 8, the present method of T-wave discrimination involves four primary steps including the initial step of defining an acceptable value range for one or more attributes (morphology, amplitude, polarity, pattern, and timing) of a reference T-wave (block 200); measuring the same one or more attributes (morphology, amplitude, polarity, pattern, and timing) of the sensed T-wave (block 202); comparing the sensed T-wave attributes to the reference T-wave attributes (block 204); and classifying the voltage signal sensed during the capture detection window as either an evoked response, indicative of capture, or as a fusion event, which may or may not indicate capture (block 206).

For purposes of the present disclosure, the morphology of the T-wave refers to particular features relating to the form and structure of the T-wave waveform at a particular moment in time. For example, the slope of the T-wave and/or the amplitude of the T-wave at any identified moment in time may be included as part of the morphology of the T-wave. The pattern of the T-wave refers to entire sequence (i.e. from start to finish) of the T-wave waveform. In other words, a comparison of the pattern of T-waves involves a comparison of the entire waveform against the reference T-wave template waveform. Lastly, the timing of the T-wave refers to the time interval between the stimulation pulse to the subsequent T-wave, that is, the stimulus to T-wave interval. It is also important to note that the step of defining the morphology, pattern, and timing of a reference T-wave, as well as the acceptable value range therefore, can alternatively be accomplished by the microprocessor at any time and stored in the memory unit associated with the microprocessor and need not, and preferably is not, done during the execution of the autocapture/autothreshold routine. Further, it is noted that T-wave attributes and acceptable value ranges therefore are patient specific.

Once the T-wave Discrimination Routine (block 130) is invoked or started (block 198), it performs the four primary steps in the identified sequence. The first step involves defining the morphology, pattern, and/or stimulus to T-wave time interval (timing) of the reference T-wave and determining what variation therefrom will be accepted as normal (block 200). This step is preferably accomplished using predefined statistical processes. For example, the reference stimulus-to-T-wave time interval is determined by monitoring a prescribed number, e.g., 3–10, of paced cardiac cycles, measuring the time interval from the V-pulse to the T-wave for each cycle, and averaging the values of the time intervals thus measured. This determination of the reference stimulus-to-T-wave time interval is preferably performed while the patient is at rest and the heart rhythm is stable. Likewise, a prescribed number of T-waves may be monitored, while the patient is at rest, to determine the reference T-wave morphology and reference T-wave pattern using related statistical processes. Similarly, and optionally simultaneously, the range of values for this (these) attribute(s) that will be considered within normal limits is determined, for example, by reference to the range of values as measured for each parameter.

The next step (block 202) of the T-wave Discrimination Routine involves measuring various attributes (morphology, pattern and timing) of a T-wave that immediately follows the voltage signal sensed during the capture detection window (block 202). Measuring the various attributes is accomplished, for example, through the analysis of a predefined portion of the IEGM signal which represents the sensed voltages and/or measuring the entire T-wave profile.

The third step (block 204) involves comparing the measured T-wave attributes to the reference T-wave attributes (block 204). Finally, the fourth step (block 206) involves classifying the sensed voltage signal as either a "true" evoked response, if the morphology of the measured T-wave, amplitude, polarity, pattern of the measured T-wave, and/or timing of the measured T-wave has not varied from the morphology, amplitude, polarity, pattern and/or timing of the reference T-wave by more than a prescribed amount (block 206), or as a fusion event, if the attribute(s) of the measured T-wave has varied from that/those of the reference T-wave by more than a prescribed amount.

Those of skill in the art are well aware of the fact that timing, amplitude, polarity, morphology and pattern of cardiac signals can vary significantly from individual to individual. With this in mind, the exact amount of variance required herein to classify the voltage signal as a fusion beat will depend upon the individual. Thus, when enabling the autocapture/autothreshold routine, the physician may either program a standard acceptable value range for each T-wave attribute, or as stated above, the acceptable value range(s) may be calculated by the pacemaker itself based upon statistical analysis of measured values of the attributes of reference T-waves. For example, if the variation observed in the morphology, pattern or timing of a sampling of reference T-waves is ±10%, then the acceptable value range for that attribute will be set, at least, to the average value for the attribute ±10%. Again, those of skill in the art are readily familiar with such a process of observing an individual patient's cardiac signal behavior and accounting for the normal variance thereof. Upon completion of the classification step (block 206), the T-wave Discrimination Routine passes the information back to the autocapture/autothreshold routine (block 208).

In particular, it is the microprocessor that is programmed to determine or analyze the character of the voltage signal that occurs during a predefined capture detection window which follows a stimulation pulse. The programmed set of instructions are preferably telemetered to the pacemaker from an external programming device via the telemetry subsystem. In order for the microprocessor to accurately identify the voltage signal, it must first an evoked response calibration step (block 104, FIG. 5) and then, in order to distinguish fusion events, define a reference T-wave morphology, pattern and/or timing and define an acceptable variation for these attributes. The microprocessor must then measure or analyze the corresponding morphology, amplitude, polarity, pattern and/or timing of a sensed T-wave. The sensed T-wave follows the voltage signal that is present during the capture detection window which follows a generated stimulation pulse. substantially from the acceptable value for that same attribute of the reference T-wave. Conversely, the microprocessor identifies the voltage signal that is sensed during the capture detection window as a fusion event whenever the measured attribute of the sensed T-wave has varied substantially from the acceptable value for that same attribute of the reference T-wave.

Figure 9:
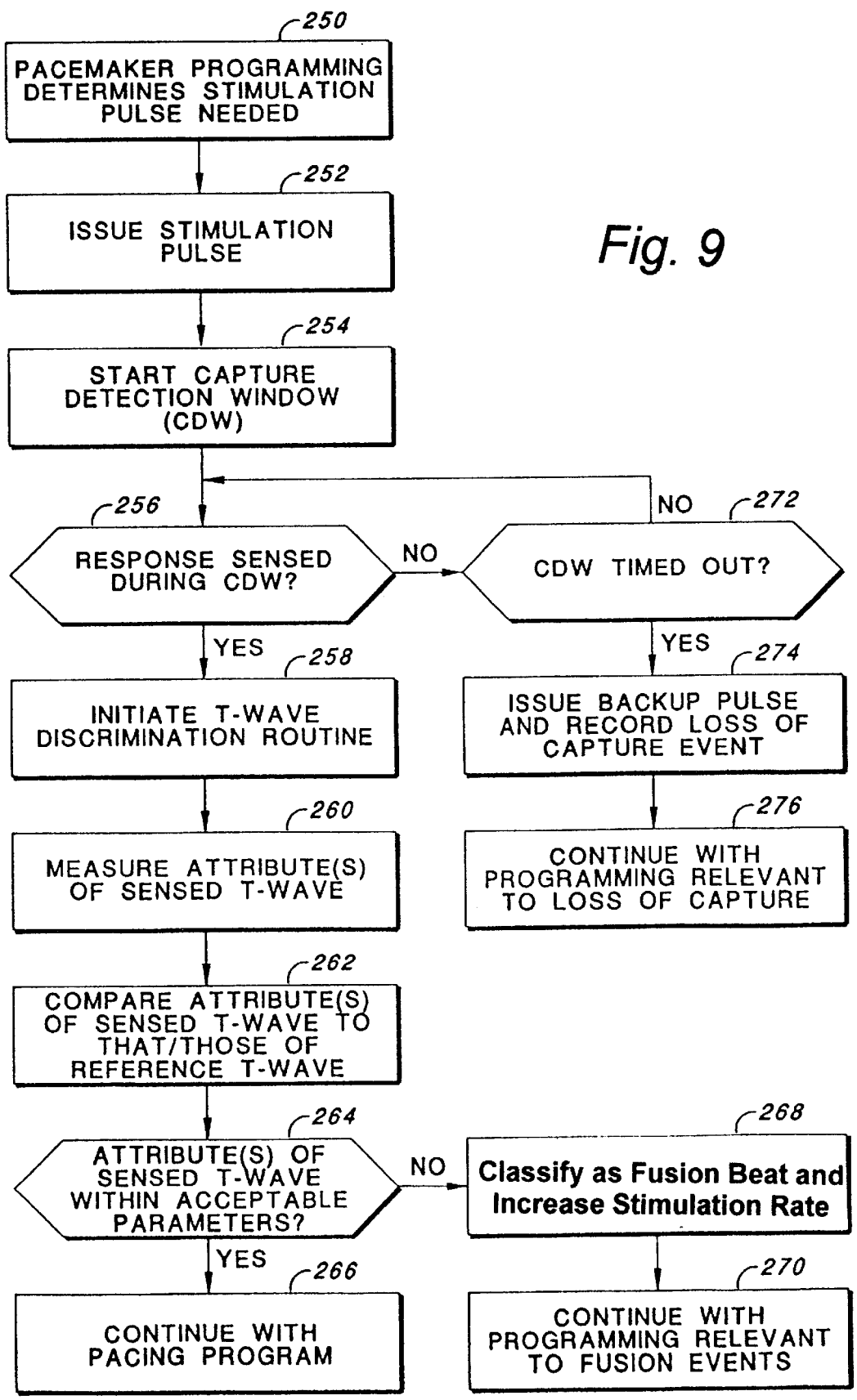
FIG. 9 is a more detailed flowchart of a preferred T-wave Discrimination Routine in accordance with the present routine.

It will be appreciated by the skilled artisan that the T-wave Discrimination Routine described herein may be employed in any pacemaker routine wherein it is desirable to verify capture by sensing a voltage waveform, or other response to a stimulation pulse, during a capture detection window. FIG. 9 illustrates such a general use of the T-wave discrimination disclosed routine herein.

FIG. 9 starts with the pacemaker programming determining that a stimulation pulse is required 250. The stimulation pulse is issued 252, and the capture detection window is started 254. It is then determined whether a response to the stimulation pulse is sensed during the capture detection window 256. If a voltage signal or other response is sensed during the capture detection window, then the T-wave Discrimination Routine is initiated 258. At this point, it is noted that the step of defining attributes of the reference T-wave, which is illustrated as block 200 on FIG. 8, may be included at this point or may be performed separately and the information stored in the pacemaker memory circuitry. Thus, while this step has been deleted from FIG. 9, it is necessary to the operation of the T-wave Discrimination Routine.

Returning then to FIG. 9, the next step is to measure one or more preselected attributes of the sensed T-wave 260 and compare the measurements with is necessary to the operation of the T-wave Discrimination Routine.

Returning then to FIG. 9, the next step is to measure one or more preselected attributes of the sensed T-wave 260 and compare the measurement(s) with the same attribute(s) of the reference T-wave 262. It is then determined whether the measured attribute(s) of the sensed T-wave are within predefined acceptable parameters 264.

If the sensed T-wave is acceptable, then the pacemaker continues with its programming that is relevant to a stimulation pulse resulting in a normal evoked response 266.

If, on the other hand, the T-wave attribute(s) is/are not within acceptable limitations, it is assumed that a fusion event has occurred and a the stimulation rate is increased so as to override the intrinsic rate and the fusion event recorded into the pacemaker memory 268.

It will, of course, be appreciated that recording such information into the pacemaker memory is not necessary to the operation of the T-wave Discrimination Routine, but may be useful to the physician or other medical personnel upon interrogation of the pacemaker. The pacemaker then initiates its programming relevant to the occurrence of such a fusion event 270.

Looking back to that portion of the routine wherein a response is or is not sensed during the capture detection window 256. If no response is sensed, then it determined whether the capture detection window has timed out 272. If it has not timed out, then the pacemaker remains sensitized to detection of a response until the capture detection window has timed out or a signal has been sensed (NO branch of 272). If the capture detection window has timed out (YES branch of 272), then a back-up pulse is issued and a loss-of-capture event recorded 274. The pacemaker then initiates its programming relevant to such a loss-of-capture event 276.

The purpose of the present T-wave Discrimination Routine is to distinguish a fusion event from an evoked response. It is noted that the invention may be practiced simply by looking for a significant change in the morphology of the T-wave that occurs immediately after a voltage signal is sensed during the capture detection window. The change in T-wave morphology relative to a defined reference T-wave morphology is a very good indication of whether a true evoked response occurred. If a true evoked response did not occur, the present voltage signal is presumed to be representative of a fusion beat. Alternatively, the invention may be practiced simply by looking for a significant change in the pattern of the T-wave as compared to a previously defined reference T-wave pattern. Again any significant change in the T-wave pattern relative to a baseline or reference T-wave pattern indicates the sensed voltage was not a true evoked response. A third alternative technique for practicing the invention is to simply measure the stimulus-to-T-wave time interval and look for a significant difference in the measured time interval compared to a reference time interval. If a significant difference does exist, it is assumed the sensed voltage signal was a fusion beat event.

It is also noted that the invention can utilize a combination of T-wave morphology and T-wave pattern discrimination criteria, T-wave morphology and T-wave timing interval discrimination criteria, T-wave pattern and T-wave timing interval discrimination criteria, or even a combination of all three T-wave discrimination criteria. In addition, whenever the invention, as practiced, relies on a change in the stimulus-to-T-wave time interval to discriminate between a fusion event and an evoked response, it is not necessary that the time interval measurements be made from the V-pulse to the peak of the subsequent T-wave. All that is required is that such time interval measurements always end at the same reference point within the T-wave, e.g. the start of the T-wave, peak of the T-wave or end of the T-wave.

From the foregoing, it should be appreciated that the present invention thus provides a method for reliably verifying capture in an implantable pacemaker by accurately discriminating a fusion event from a non-fusion event during any routine employing a capture detection window to sense capture; the method being based on an analysis and comparison of the morphology, pattern and/or timing intervals of T-waves, subsequent the detection of a voltage wave form during the capture detection window. While the invention herein disclosed has been described by means of specific embodiments and applications thereof, numerous modifications and variations could be made thereto by those skilled in the art without departing from the scope of the invention set forth in the claims or sacrificing all of its material advantages.

What is claimed is:

1. In an implantable pacemaker, a method of discriminating between a fusion event or an evoked response, the method comprising the steps of:
   selectively generating stimulation and backup pulses at a predetermined rate;
   sensing a first response during a first detection window following a stimulation pulse;
   sensing T-waves during a second detection window that follows the stimulation pulse;
   determining if a current T-wave corresponds to a true evoked response or a fusion beat; and
   increasing the stimulation pulse rate when fusion beats occur thereby minimizing the generation of backup pulses subsequent to the generation of stimulation pulses.

2. The method of claim 1, wherein the step of determining if the current T-wave corresponds to a true evoked response or a fusion beat comprises the steps of:
   determining a reference T-wave;
   defining an acceptable value range for an attribute of the reference T-wave;
   measuring the same attribute of the current T-wave;
   defining the first sensed response as an evoked response when the measured attribute of the current T-wave is within the acceptable value range of the reference T-wave attribute; and
   defining the evoked response as a fusion event when the measured attribute of the current T-wave is not within the acceptable value range of the reference T-wave attribute.

3. The method of claim 2, wherein the step of defining an acceptable range comprises the step of:
   automatically performing statistical analysis of a plurality of T-waves to determine an acceptable value range for the at least one attribute of the reference T-wave.

4. The method of claim 3, wherein the attribute is selected from the group consisting of T-wave morphology, amplitude, polarity, pattern and stimulus to T-wave time interval.

5. The method of claim 4, wherein more than one T-wave attributes are used to define the reference T-wave and the same more than one attributes are measured for the current T-wave.

6. A method for discriminating a fusion event from an evoked response in an implantable pacemaker during an autocapture/autothreshold routine, wherein the autocapture/autothreshold routine adjusts the output energy of stimulation pulses in response to sensing and not sensing a response to a stimulation pulse, the method comprising the steps of:
   defining at least one attribute of a reference T-wave wherein the definition includes an acceptable variance in that attribute;
   sensing a first response corresponding to a stimulation pulse delivered during the autocapture/autothreshold routine;
   measuring the same at least one attribute as was defined for the reference T-wave for a T-wave corresponding to the stimulation pulse;
   comparing the at least one attribute of the T-wave to the same at least one attribute of the reference T-wave;
   defining the first sensed response to the stimulation pulse as an evoked response if the measured attribute of the T-wave is within the acceptable variance of the reference T-wave definition; and
   defining the first sensed response to the stimulation pulse as a fusion event if the measured attribute of the T-wave is not within the acceptable variance of the reference T-wave definition.

7. The method of claim 6, further comprising the step of:
   blocking the autocapture/autothreshold routines from making any adjustments to the output energy of the stimulus pulses when the first sensed response is defined as a fusion beat; and
   increasing a rate of the stimulation pulses so as to overdrive the fusion beat.

8. The method of claim 6, wherein the at least one attribute of the reference T-Wave and measured T-wave is selected from the group consisting of morphology, amplitude, polarity, pattern and stimulus to T-wave time interval.

9. In an implantable pacemaker, a method for classifying a voltage signal sensed in response to a stimulation pulse as an evoked response or a fusion beat, the method comprising the steps of:

generating stimulation pulses to a patient's heart;

defining an acceptable value range for at least one attribute of the patient's T-waves, said range extending a predetermined amount above and below a prescribed reference value;

sensing the voltage signal in response to a stimulation pulse;

sensing the T-wave that follows the sensed voltage signal;

measuring the at least one attribute of the sensed T-wave;

classifying the sensed voltage signal as a fusion beat if the measured attribute of the T-wave is beyond the prescribed acceptable value range; and classifying the sensed voltage signal as an evoked response if the measured attribute of the T-wave is within the prescribed acceptable value range.

10. The method of claim 9, wherein the at least one attribute of the T-wave is selected from the group consisting of T-wave pattern, amplitude, polarity, morphology and stimulus to T-wave timing interval.

11. The method of claim 9, wherein the step of prescribing an acceptable value range for the at least one attribute of T-waves comprises:

detecting a plurality of T-waves and setting the prescribed reference value as the average value of such attribute detected in the plurality of T-waves; and determining an acceptable value range for the at least one attribute comprising detecting the variation of the attribute from the prescribed reference value in the plurality of T-waves and setting the acceptable value range to such variation.

12. An implantable stimulation device, comprising:

a pulse generator which generates stimulation pulses at a predetermined rate;

a timing circuit, triggered by the generation of a stimulation pulse, that defines a first and second detection window;

a sensing circuit that senses a first response during a first detection window following a stimulation pulse and a second response during the second detection window; and a processor circuit, coupled to the sensing circuit, that determines if a T-wave which is sensed in the second detection window corresponds to a true evoked response or a fusion beat, the processor circuit further having means for increasing the rate when fusion beats occur, the processor circuit still further having autocapture/autothreshold routine means operative to adjust the output energy of stimulation pulses in response to sensing and not sensing a response to a stimulation pulse.

13. The implantable stimulation device of claim 12, further comprising:

means for measuring a reference T-wave;

means for measuring the same attribute of the current T-wave; and means for comparing the reference T-wave to the current T-wave.

14. The implantable stimulation device of claim 13, wherein processor circuit comprises:

means for defining an acceptable value range for an attribute of the reference T-wave;

means for defining the first sensed response as an evoked response when the measured attribute of the current T-wave is within the acceptable value range of the reference T-wave attribute; and means for defining the evoked response as a fusion event when the measured attribute of the current T-wave is not within the acceptable value range of the reference T-wave attribute.

15. The implantable stimulation device of claim 14, wherein the at least one attribute of the reference T-wave and the measured T-wave is selected from the group consisting of morphology, amplitude, polarity, pattern and stimulus to T-wave time interval.

16. The implantable stimulation device of claim 15, wherein at least two attributes of the reference T-wave are defined and the same at least two attributes of the measured T-wave are measured.

17. The implantable stimulation device of claim 16, wherein the defined attributes of the reference T-wave and the measured attributes of the measured T-wave comprise morphology, amplitude, polarity, pattern and stimulus to T-wave time interval.

* * * * *